US012649769B2

(12) United States Patent
Zhou

(10) Patent No.: US 12,649,769 B2
(45) Date of Patent: Jun. 9, 2026

(54) RECOMBINANT HUMAN NEUREGULIN DERIVATIVES AND USE THEREOF

(71) Applicant: Zensun (Shanghai) Science & Technology, Co., Ltd., Shanghai (CN)

(72) Inventor: Mingdong Zhou, Shanghai (CN)

(73) Assignee: Zensun (Shanghai) Science & Technology, Co., Ltd., Shanghai (CN)

( * ) Notice: Subject to any disclaimer, the term of this patent is extended or adjusted under 35 U.S.C. 154(b) by 1031 days.

(21) Appl. No.: 17/642,855

(22) PCT Filed: Sep. 14, 2020

(86) PCT No.: PCT/CN2020/114955
§ 371 (c)(1),
(2) Date: Oct. 27, 2022

(87) PCT Pub. No.: WO2021/052277
PCT Pub. Date: Mar. 25, 2021

(65) Prior Publication Data
US 2023/0057622 A1      Feb. 23, 2023

(30) Foreign Application Priority Data

Sep. 16, 2019   (CN) ......................... 201910873003.9
Sep. 11, 2020   (CN) ......................... 202010955006.X

(51) Int. Cl.
*C07K 14/475*      (2006.01)
*A61P 9/00*      (2006.01)
*C07K 14/55*      (2006.01)

(52) U.S. Cl.
CPC ............ *C07K 14/4756* (2013.01); *A61P 9/00* (2018.01); *C07K 14/55* (2013.01); *C07K 2319/30* (2013.01)

(58) Field of Classification Search
CPC ................................................. C07K 14/4756
See application file for complete search history.

(56) References Cited

U.S. PATENT DOCUMENTS

| | | | |
|---|---|---|---|
| 7,271,149 B2 | 9/2007 | Glaesner et al. |
| 10,294,287 B2 | 5/2019 | Greve |
| 10,441,633 B2 | 10/2019 | Mingdong |
| 10,702,585 B2 | 7/2020 | Mingdong |
| 11,235,031 B2 | 2/2022 | Caggiano et al. |
| 11,253,573 B2 | 2/2022 | Mingdong |
| 2016/0165860 A1 | 6/2016 | Ait-Ali et al. |
| 2019/0202881 A1 | 7/2019 | Greve |

FOREIGN PATENT DOCUMENTS

| | | | |
|---|---|---|---|
| CN | 1276381 A | 12/2000 |
| CN | 104623633 A | 5/2015 |
| CN | 108623672 A | 10/2018 |
| EP | 3090756 A1 | 11/2016 |
| JP | 2017-502969 | 1/2017 |
| KR | 2008-0085082 | 9/2008 |
| KR | 2014-0076570 | 6/2014 |
| KR | 2016-0105443 | 9/2016 |
| KR | 2017-0091096 | 8/2017 |
| KR | 2018-0100237 | 9/2018 |
| WO | WO 2013053076 A1 | 4/2013 |
| WO | WO 2016045493 A1 | 3/2016 |
| WO | WO 2016069574 A1 | 5/2016 |
| WO | WO 2018167320 A1 | 9/2018 |
| WO | WO 2019143272 A1 | 7/2019 |
| WO | WO 2019200033 A1 | 10/2019 |

OTHER PUBLICATIONS

International Search Report mailed Dec. 10, 2020 for International Application No. PCT/CN2020/114955 (26 pages).
Niranjana et al.,2016, "Fc IgG1 heavy chain constant region, partial [*Homo sapiens*], " NCBI (1 page).
Wikipedia, "Signal Peptide," As accessed on Aug. 27, 2025 (3 pages). Available online at: https://en.wikipedia.org/w/index.php?title=Signal_peptide&oldid=881137750.
Zhang et al., 2018, "NRG1-Fc improves metabolic health via dual hepatic and central action," JCI Insight 3(5):1-12.

*Primary Examiner* — Prema M Mertz

(74) *Attorney, Agent, or Firm* — Jones Day

(57)      ABSTRACT

Disclosed is a use of recombinant human neuregulin derivatives in preparing a medicine for preventing, treating, or reducing the progression of cardiovascular diseases in mammals. In particular, the present invention relates to a novel recombinant human NRG-FC protein and a use thereof in the treatment of cardiovascular diseases. The protein has a prolonged half-life and enhanced biological activity.

2 Claims, 3 Drawing Sheets

Specification includes a Sequence Listing.

RECOMBINANT HUMAN NEUREGULIN DERIVATIVES AND USE THEREOF

CROSS-REFERENCE TO RELATED APPLICATIONS

This application is a U.S. National Stage Application under 35 U.S.C. § 371 of International Patent Application No. PCT/CN2020/114955, filed Sep. 14, 2020, which claims priority to Chinese Patent Application No. 202010955006.X, filed Sep. 11, 2020, and Chinese Patent Application No. 201910873003.9, filed Sep. 16, 2019, the disclosure of each of which is incorporated by reference herein in its entirety.

SEQUENCE LISTING

This application incorporates by reference in its entirety the Computer Readable Form of a Sequence Listing in ASCII text format submitted via EFS-Web. The Sequence Listing text file submitted via EFS-Web is entitled "11748-104-999_SEQ_LISTING.txt," was created on Mar. 4, 2022 and is 7,274 bytes in size.

FIELD OF THE INVENTION

The present invention relates to the use of a recombinant human neuregulin derivative for the preparation of a drug for preventing, treating or relieving cardiovascular diseases in mammals. In particular, the present invention relates to a novel recombinant human NRG-Fc protein and its use for treating cardiovascular diseases.

BACKGROUND OF THE INVENTION

Neuregulin (NRG; heregulin, HRG), which is also known as a glial growth factor (GGF) or new differentiation factor (NDF), is a glycoprotein with a molecular weight of about 44 KD, and as a ligand for the ErbB family of receptor tyrosine kinases, it transmits signals among cells. The NRG family consists of four members, including NRG1, NRG2, NRG3, and NRG4 (Falls et al., Exp Cell Res. 284: 14-30, 2003). NRG1 plays an important role in the nervous system, heart and breast. There is also evidence that NRG1 signaling plays a role in the development and function of some other organ systems and the pathogenesis of human diseases including schizophrenia and breast cancer. NRG1 has many isomers. The study on mutant mice (knockout mice) shows that different isomers in the N-terminus region or epidermal growth factor (EGF)-like domain have different functions in vivo. The present invention is based on NRG1β.

NRG1β is a transmembrane protein (Holmes et al., Science 256, 1205-1210, 1992). The extramembranous part is N-terminus, including the Ig-like domain and EGF-like domain, while the intramembranous part is C-terminus. Under the action of metalloproteinases (MMP) in extracellular matrix (ECM), the extramembranous part of NRG can be clipped off by enzymes and released in a free state, thus promoting its binding to ErbB receptors on the surface of peripheral cells, activating relevant cell signaling.

The ErbB receptor family is also divided into four categories, including ErbB1, ErbB2, ErbB3 and ErbB4, all of which are transmembrane proteins with a molecular weight of 180-185 KD. Except ErbB2, they all contain a ligand-binding domain at extramembranous N-terminus; except ErbB3, they all contain protein tyrosine kinases at intramembranous C-terminus. ErbB1 is an EGF receptor, while both ErbB3 and ErbB4 are NRG receptors. Among NRG receptors, only ErbB2 and ErbB4 are highly expressed in the heart (Yarden et al., Nat Rev. Mol Cell Biol, 2: 127-137, 2001).

When NRG binds to the extramembranous part of ErbB3 or ErbB4, ErbB3 or ErbB4 will form a heterodimer with other ErbB receptors (usually including ErbB2), or ErbB4 forms a homodimer by itself. As a result, the intramembranous part of the receptor is phosphorylated (Yarden et al., Nat Rev. Mol Cell Biol, 2: 127-137, 2001). The phosphorylated intramembranous part can further bind to a variety of signaling proteins in the cells, thereby activating the downstream ERK or AKT signaling pathway and causing a series of cell reactions, including stimulating or inhibiting cell proliferation, cell apoptosis, cell migration, cell differentiation or cell adhesion.

NRG is of particular importance for heart development (WO0037095, CN1276381, WO03099300, WO9426298, U.S. Pat. No. 6,444,642, WO9918976, WO0064400, Zhao et al., J. Biol. Chem. 273, 10261-10269, 1998). At the early stage of embryonic development, the expression of NRG is mainly confined to endocardium, and then is released to peripheral myocardial cells through the paracrine pathway and binds to the extramembranous part of the PTK receptor ErbB4 on the cell membrane. Further, ErbB4 forms a heterodimer with ErbB2. The formation and activation of ErbB4/ErbB2 complex is essential for trabeculation in the sponge-like heart at the early stage. The deletion of any of the three protein genes, i.e. NRG ErbB4 and ErbB2, is bound to deprive the embryo of trabecula and make it perish in the uterus at the early stage of development. WO0037095 show that a given concentration of NRG can continuously activate the ERK signaling pathway, promote the growth and differentiation of myocardial cells, guide the reconstruction of the sarcomere and cytoskeleton at myocardial cell adhesion, improve the structure of myocardial cells, and enhance the contraction of myocardial cells. WO0037095 and WO003099300 also teach that NRG can be used to detect, diagnose and treat various cardiovascular diseases.

Some prior art references relating to the present invention are listed below: 1. Cardiac muscle function and manipulation: WO0037095; 2. Neuregulin, a growth factor and a new application of its analogue: CN1276381; 3. Neuregulin based methods and composition for treating cardiovascular diseases: WO03099300; 4. Zhao Y Y, Sawyer D R, Baliga R R, Opel D J, Han X, Marchionni M A and Kelly R A. Neuregulins Promote Survival and Growth of Cardiac Myocytes. J. Biol. Chem. 273, 10261-10269 (1998); 5. Methods for treating Muscle Diseases and Disorder: WO9426298; 6. Methods of incrementing myotube formation or survival or muscle cell mitogenesis, differentiation or survival using a neuregulin: US6,444,642.7. Therapeutic methods comprising use of a neuregulin: WO9918976; 8. Methods for treating congestive heart failure: WO0064400; 9. Holmes W E, Sliwkowski M X, Akita R W, Henzel W J, Lee J, Park J W, Yansura D, Abadi N, Raab H, Lewis G D, et al. Identification of heregulin, a specific activator p185erbB2. Science 256, 1205-1210 (1992); 10. Falls D L. Neuregulins: functions, forms and signaling strategies. Experimental Cell Research, 284, 14-30 (2003). 11. Yarden Y, Sliwkowski X. Untangling the ErbB signaling Network. Nature Reviews: Molecular Cell Biology, 2127-137 (2001).

A promising new therapy involves application of neuregulin in patients with cardiovascular diseases (hereinafter referred to as "NRG"). Existing studies show that there are about 50 to 64 amino acids in the EGF-like domain of NRG1, and that they are fully capable of binding to and activating these receptors. Previous studies show that NRG-1p can directly bind to ErbB3 and ErbB4 with high affinity for them. The orphan receptor ErbB2 can form a heterodimer with ErbB3 or ErbB4, and its affinity is higher than that of the ErbB3 or ErbB4 homodimer. The research results of neurodevelopment indicate that the formation of the sympathetic nervous system requires a complete NRG-1 β, ErbB2 and ErbB3 signal transduction system. After targeted destruction of NRG-1 β, ErbB2 or ErbB4, the embryo perishes due to cardiac development defects. Recent studies also highlight the important role of NRG-1 β, ErbB2 and ErbB4 in cardiovascular development and the maintenance of normal cardiac function in adults. The research shows that NRG-1 β can enhance the tissue structure of sarcomere in adult myocardial cells. Short-term application of a recombinant NRG-1 β EGF-like domain can significantly improve or prevent the deterioration of myocardial functions in three different animal models of heart failure. More importantly, NRG-1 β can significantly prolong the survival of animals with heart failure. However, it is still necessary to further optimize or improve NRG in order to find a more effective neuroregulatory polypeptide protein, which can be used to prevent, treat or alleviate cardiovascular diseases.

SUMMARY OF THE INVENTION

The present invention relates to the use of a recombinant human neuregulin derivative for the preparation of a drug for preventing, treating or relieving cardiovascular diseases in mammals. In particular, the present invention relates to a new recombinant human NRG-Fc protein and its use for treating cardiovascular diseases. In some embodiments, the mammal is a human being. In some embodiments, the individual is a human being.

In the first aspect, the prevention invention provides NRG fusion polypeptides. In some embodiments, the NRG fusion polypeptide comprises an EGF-like domain of NRG In some embodiments, the NRG fusion polypeptide comprises an EGF-like domain of an NRG1β2 isomer. In some embodiments, the NRG fusion polypeptide comprises an amino acid sequence of SEQ ID NO: 1. In some embodiments, the NRG fusion polypeptide comprises an amino acid sequence of an SEQ ID NO: 1 analogue thereof. In some embodiments, the NRG fusion polypeptide comprises an amino acid sequence of Ig Fc. In some embodiments, the NRG fusion polypeptide comprises an amino acid sequence of an Ig Fc analogue thereof. In some embodiments, the NRG fusion polypeptide comprises an amino acid sequence of IgG Fc. In some embodiments, the NRG fusion polypeptide comprises an amino acid sequence of an IgG Fc analogue thereof. In some embodiments, the NRG fusion polypeptide comprises an amino acid sequence of IgG1 Fc. In some embodiments, the NRG fusion polypeptide comprises an amino acid sequence of IgG4 Fc. In some embodiments, the NRG fusion polypeptide comprises an amino acid sequence of an IgG1 Fc analogue thereof. In some embodiments, the NRG fusion polypeptide comprises an amino acid sequence of an IgG4 Fc analogue thereof. In some embodiments, the NRG fusion polypeptide comprises an amino acid sequence of an IL-2 signal peptide, and an amino acid sequence of the IL-2 signal peptide is cleaved during extracellular secretion of the recombinantly prepared. In some embodiments, the NRG fusion polypeptide comprises an amino acid sequence of the EGF-like domain of NRG and IgG Fc. In some embodiments, the NRG fusion polypeptide comprises an amino acid sequence of the linker peptide, and the EGF-like domain of NRG is fused with IgG Fc through the peptide linker. In some embodiments, the NRG fusion polypeptide comprises an amino acid sequence of SEQ ID NO: 2. In some embodiments, the NRG fusion polypeptide comprises an amino acid sequence of SEQ ID NO: 3.

Some NRG fusion polypeptides contain the following amino acid sequence: Ser His Leu Val Lys Cys Ala Glu Lys Glu Lys Thr Phe Cys Val Asn Gly Glu Cys Phe Met Val Lys Asp Leu Ser Asn Pro Arg Tyr Leu Cys Lys Pro Asn Pro Asn Asp Arg Cys Gln Asn Tyr Val Met Ala Ser Phe Tyr Lys Ala Glu Glu Leu Tyr Gln Gln (SEQ ID NO: 1), i.e., human NRG-1 amino acid sequence 177-237.

Some NRG fusion polypeptides contain the following amino acid sequence: Ser His Leu Val Lys Cys Ala Glu Lys Glu Lys Thr Phe Cys Val Asn Gly Glu Cys Phe Met Val Lys AspLeu Ser Asn Pro Ser Arg Tyr Leu Cys Lys Pro Asn Glu Pro Thr Gly Asp Arg Cys Gln Asn Tyr Val Met Ala Ala Glu Glu Leu Tyr Gln Gly Gly Gly Gly Gly Gly Gly Gly Gly Ser Glass Y Gly Gly Gly Ser Glu Pro Lys Ser Cys Asp Lys Thr His Thr Cys Pro Pro Cys Pro Ala Pro Glu Leu Leu Gly Gly Pro Ser Val Phe Phe Pro Lys Pro Lys Asp Thr Leu Met Ile Ser Arg Thr Pro Glu Val Thr Cys Val Val Asp Pro Glu Val Lys Phe Asn Tryr Val Asp Glyr Val Val Lys Pro Arg Glu Glys Lu Gln Tyr Asn Ser Thr Tyr Arg Val Val Ser Val Leu Thr Val Leu His Gln Asp Trp Leu Asn Gly Lys Glu Tyr Lys Cys Val Ser Asn Lys Ala Leu Pro Ala Pro Ile Glu Lys Ala Lys Gly Gln Pro Arg Glu Pro Gln Val Tyr Thr Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gln Gly Asn Val Phe Ser Cys Ser Val Met His Glu Ala Leu His Asn Tyr Thr Gln Lys Ser Leu Leu Ser Pro Gly Lys (SEQ ID NO: 2).

Some NRG fusion polypeptides contain the following amino acid sequence: Ser His Leu Val Lys Cys Ala Glu Lys Glu Lys Thr Phe Cys Val Asn Gly Glu Cys Phe Met Val Lys Asp Leu Ser Asn Pro Ser Arg Tyr Leu Cys Lys Pro Pro Asn Glu Pro Thr Gly Asp Arg Tyr Val Met Ala Ser Phe Tyr Lys Ala Glu Glu Leu Tyr Gln Gly Gly Gly Gly Gly Gly Gly Gly Gly Gly Ser Glass Y Gly Gly Gly Ser Glu Ser Lys Tyr Gly Pro Pro Cys Pro Pro Cys Pro Ala Pro Glu Phe Glu Gly Gly Pro Ser Val Phe Phe Pro Lys Pro Lys Asp Thr Leu Met Ile Ser Arg Thr Pro Glu Val Thr Cys Val Val Asp Val Ser Gln Asp Pro Glu Gln Phe Asn Trp Tyr Val Asp Gly Val Val Gln n Phe Asn Ser Thr Tyr Arg Val Val Ser Val Leu Thr Val Leu His Gln Asp Trp Leu Asn Gly Lys Glu Tyr Lys Cys Val Ser Asn Lys Gly Leu Pro Ser Ser Lys Ala Lys Gly Gln Pro Arg Glu Pro Gln Glu Glu Met Thr Lys Asn Gln Val Ser Leu Thr Cys Leu Val Lys Gly Phe Tyr Pro Ser Asn P Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn Tyr Thr Gln Lys Ser Leu Ser Leu Leu Gly Lys Ala Ser (SEQ ID NO: 3).

The NRG fusion polypeptide can be prepared in accordance with any related techniques known in the art. A typical technique for preparing a NRG fusion polypeptide is provided herein. In some embodiments, an NRG fusion polypeptide can be recombinant.

In the second aspect, the present invention provides a nucleic acid, vector and host cell associated with an NRG fusion polypeptide. The nucleic acid or its complementary sequence encodes an NRG fusion polypeptide or a fragment thereof. The nucleic acid can be double-stranded or single-stranded DNA or RNA that can be inserted into a suitable vector for proliferation and expression of the NRG fusion polypeptide. The modified vector is transferred into a suitable host cell, such as a host cell that can express the recombinant NRG fusion polypeptide.

In the third aspect, the present invention provides a therapeutic and non-therapeutic application of the NRG fusion polypeptide. In particular, the present invention provides a method for applying the NRG fusion polypeptide to preventing, treating or alleviating cardiac diseases and disorders. Accordingly, the present invention provides a pharmaceutical formulation that comprises the NRG fusion polypeptide and a therapeutic method therefor.

In the fourth aspect, the present invention provides a method for treating heart failure in mammals. In some embodiments, the method comprises a step of injecting the NRG fusion polypeptide into a mammal.

In the fifth aspect, the present invention provides a method for inducing phosphorylation of an ErbB receptor in cells. In some embodiments, the method comprises a step of exposing the NRG fusion polypeptide to cells.

In the sixth aspect, the present invention provides a method for inducing and maintaining activation of the AKT signaling pathway in cardiac cells. In some embodiments, the method comprises a step of exposing the NRG fusion polypeptide to cardiac cells.

In the seventh aspect, the present invention provides a method for inducing and maintaining activation of the ERK signaling pathway in cardiac cells. In some embodiments, the method comprises a step of exposing the NRG fusion polypeptide to cardiac cells.

DETAILED DESCRIPTION OF THE INVENTION

A. Explanations

Unless otherwise defined, all the scientific and technical terms used herein have the same meaning as is understood by those skilled in the art. All the patent documents, patent application documents, published patent documents and other publications mentioned herein are incorporated herein by reference in their entirety. If any definition covered in the present section has a meaning different from what is explained in any of the aforesaid patent documents, patent application documents, published patent documents, or other publication, the explanation given in the present section shall prevail.

Unless otherwise specified, "a/an", as used herein, means "at least one" or "one or more than one".

EGF-like domain, as used herein, refers to a polypeptide segment encoded by a neuregulin gene that can bind to and activate ErbB2, ErbB3, ErbB4 or their heterodimer or homodimer, and has structural similarity to the EGF receptor binding domain described in the following references: WO 00/64400; Holmes et al., Science, 256:1205-1210 (1992); U.S. Pat. Nos. 5,530,109 and 5,716,930; Hijazi et al., Int. J. Oncol., 13: 1061-1067 (1998); Chang et al., Nature, 387: 509-512 (1997); Carraway et al., Nature, 387:512-516 (1997); Higashiyama et al., J. Biochem., 122:675-680 (1997); as well as WO 97/09425. The above content is incorporated herein by reference in its entirety. In some embodiments, the EGF-like domain binds to and activates ErbB2/ErbB4 or ErbB2/ErbB3 heterodimer. In some embodiments, the EGF-like domain comprises the amino acids in the NRG-1 receptor binding domain. In some embodiments, the EGF-like domain refers to the 177-226, 177-237, or 177-240 amino acids of NRG-1. In some embodiments, the EGF-like domain comprises the amino acids in the NRG-2 receptor binding domain. In some embodiments, the EGF-like domain comprises the amino acids in the NRG-3 receptor binding domain. In some embodiments, the EGF-like domain comprises the amino acids in the NRG-4 receptor binding domain.

Fc amino acid sequence, as used herein, can be selected from human IgG-1 heavy chain. See Ellison, J. W. et al., Nucleic Acids Research, 10: 4071-4079 (1982), or any Fc sequence known in the art (e.g., other IgG types, including but not limited to, IgG-2, IgG-3 and IgG-4, or other immunoglobulins). It is well known that the Fc fragment of antibody consists of monomeric polypeptide segments, and the monomeric polypeptide segments can be linked together through a disulfide bond or non-covalent bond into a dimer or polymer. There are 1-4 intramolecular disulfide bonds formed between the monomer subunits of a natural Fc molecule, depending on the type of the antibody involved (e.g., IgG, IgA, IgE) or subtype (e.g., IgG-1, IgG-2, IgG-3, IgA-1, IgA-2). The term "Fc", as used herein, can represent the monomer, dimer and polymer of the Fc molecule. It should be noted that when a suitable cysteine residue exists, the Fc monomer automatically forms a dimer unless a specific condition exists which prevents the formation of a disulfide bond and thereby prevents dimer formation. Even if cysteine, which can normally form a disulfide bond in the Fc dimer, is deleted or substituted with another residue, a monomer chain can usually be dimerized by non-covalent interaction. The term "Fc", as used herein, is used to signify any of the following forms: natural monomer, natural dimer (disulfide bond linkage), modified dimer (disulfide bond and/or non-covalent linkage), and modified monomer (i.e. derivatives).

Fc analogues, as used herein, including variants, analogues or derivatives, can be constructed by, for example, performing multiple substitutions of residues or sequences. Fc analogues include insertional analogues, deletion analogues, substitution analogues and the like.

A variant (or analogue) polypeptide contains an insertional variation, wherein one or more amino acid residues are added to the Fc amino acid sequence. The insertion site can be either terminus or both terminuses of the protein or an internal domain of the Fc amino acid sequence. An insertional variant obtained from the addition of a residue at either terminus or both terminuses of the protein can include, for example, a fusion protein and a protein that comprises amino acid markers.

In an Fc-deletion variant (or analogue), one or more amino acid residues in the Fc polypeptide are deleted. Deletion can occur at one end or both ends of the Fc polypeptide, and one or more residues can be deleted from the Fc amino acid sequence. Therefore, the deletion variant comprises all segments of the Fc polypeptide sequence.

In an Fc substitution variant (or analogue), one or more amino acid residues of the Fc polypeptide are deleted and substituted with other residues. On the one hand, autogenetic substitutions are conservative, but the present invention also comprises non-conservative substitutions.

For example, in order to prevent some or all disulfide bond cross-linking in the Fc sequence, the cysteine residues can be deleted or substituted with other amino acids. These cysteine residues can be deleted separately, or one or more of these cysteine residues can be substituted with other amino acids such as alanine or serine. As shown in another embodiment, by introducing amino substitution, modification can also (1) delete the Fc receptor binding site; (2) delete the complement (Clq) binding site; and/or (3) delete the antibody dependent cell-mediated cytotoxicity (ADCC) site; these sites are well known in the art, and any well-known substitution within the Fc range can be used. For example, see Molecular Immunology, Vol. 29, Issue 5, 633-639 (1992), i.e., the ADCC site on IgG1.

Similarly, one or more tyrosine residues can also be substituted with phenylalanine residues. In addition, the insertional, deletion and/or substitutional variants of other amino acids are also under consideration and included within the scope of the present invention. Conservative amino acid substitutions are normally preferred. In addition, a change can take place in the form of an amino acid, such as a mimic peptide or D-amino acid.

Signal peptide: Also known as leader peptide, it is normally a polypeptide segment with a length of 15~30 amino acids existing at the N-terminus of a protein molecule, and it enables the protein to secrete through the cell membrane. After protein secretion, the signal sequence is removed.

The signal peptide sequence, as used herein, comprises the secretory signal peptides used in the expression of mammalian cells and insect cells/baculovirus expression system, such as melittin, IFN and IL-2 signal peptide.

IL-2 signal peptide, as used herein, has the following amino acid sequence: Met Tyr Arg Met Gln Leu Leu Ser Cys Ile Ala Leu Ser Leu Ala Leu Val Thr Asn Ser (SEQ ID NO: 4) or an amino acid sequence of an analogue thereof. By adding the signal peptide sequence to guide the secretion of fusion polypeptide, the secretion efficiency can be improved and the downstream purification process can be simplified. Moreover, it plays a positive role in maintaining the stability and activity of the fusion peptide.

Linker peptide: Linker peptide is a sequence that links fused protein segments in a fusion protein.

Linker peptides used herein are divided into two types: 1. Flexible linkers, such as (GGGGS)n(n<=6); 2. rigid linkers, such as (EAAAK)n(n<=6) or (XP)n, where X is preferably alanine, glutamic acid or lysine, etc.

A linker peptide, as used herein, has the following amino acid sequence: Gly Gly Gly Gly Ser Gly Gly Gly Ser Gly Gly Gly Ser (SEQ ID NO: 5) or an amino acid sequence of an analogue thereof.

An "effective dose" of an active ingredient for the treatment of a particular disease, as used herein, is a dose that is effective enough to improve or relieve the symptoms of the disease in one way or another. This dose may cure the disease, but in a typical case, it is used to improve the symptoms of the disease.

An "active ingredient", as used herein, is any substance used to diagnose, cure, alleviate, treat or prevent a disease in humans or other animals or enhance physical or mental health.

"Improvement" of a specific disorder, as used herein, means permanent or temporary, sustained or transient alleviation of a symptom by use of a specific active reagent, and the alleviation is attributed to or associated with the use of the reagent.

"Treatment", as used herein, refers to any way in which discomfort, a disorder or a disease symptom is improved or changed for the better. The effect can be prophylactic, e.g., a disease or its symptoms is completely or partially prevented. The effect can also be therapeutic, e.g., a disease and/or its adverse impact are partially or completely cured. Treatment also comprises any pharmaceutical use of a composition described herein.

A "vector (or plasmid)", as used herein, refers to a dispersed component used to introduce heterologous DNA into a cell for expression or replication therein. Selection and use of these vectors are familiar to those skilled in the art. An expression vector comprises a vector capable of expressing the DNA linked to a regulatory sequence, such as a promotor region, which can influence the expression of these DNA fragments. Therefore, an expression vector refers to a recombinant DNA or RNA component, such as a plasmid, bacteriophage, recombinant virus or other vectors, which cause the expression of cloned DNA when introduced into a proper host cell. A suitable expression vector is well known to those skilled in the art, including a vector that is replicated in a eukaryotic cell and/or prokaryotic cell and a vector that remains in a free state or is integrated into a host cell genome.

"Myocardial cell differentiation", as used herein, refers to a state characterized by a reduction of more than 10% in DNA synthesis, inhibition of DNA synthesis stimulated by other factors by more than 10%, ordered sarcomere binding and cell-cell adhesion, sustained activation of MAP kinases, and enhanced expression of p21 Cip1, as shown below. See WO00/37095 for further discussion, and its content is incorporated herein by reference in its entirety.

"Ejection fraction" or "EF", as used herein, refers to the proportion of blood pumped from the full left ventricle in one heartbeat. It can be defined by the following formula: (left ventricular end-diastolic volume (LVEDV)–left ventricular end-systolic volume (LVESV))/LVEDV.

"Fractional shortening" or "FS", as used herein, refers to the ratio of the left ventricular diameter in a systolic state to the left ventricular diameter in a diastolic state. It can be defined by the following formula: (left ventricular diastolic diameter (LVDD)–left ventricular systolic diameter (LVSD))/LVDD.

"Cardiovascular disease", as used herein, refers to heart failure, myocardial infarction, coronary atherosclerotic heart disease, arrhythmia, myocarditis, valvular heart disease, infective endocarditis, pericardial disease, ischemic heart disease, congenital heart disease, etc. These diseases tend to induce myocardial injury.

"Myocardial injury", as used herein, refers to myocardial injury caused by a pathological cardiac disease. Myocardial injury tends to induce cardiac dysfunction, thereby affecting human health. The pathogenesis of myocardial injury involves the production of oxygen free radicals, calcium ion overload, an inflammatory reaction caused by neutrophil infiltration in an injured region, apoptosis or necrosis of myocardial cells, tissue metabolism disorders caused by energy supply disorders, abnormal cardiac electric signal transduction, cholesterol accumulation, formation of atherosclerotic plaques, and some other pathophysiological changes.

"Heart failure" or "HF", as used herein, refers to a cardiac dysfunction which disenables the heart to pump blood at the rate required by metabolic tissues. Heart failure comprises many morbid states such as congestive heart failure (CHF), myocardial infarction, tachyarrhythmia, familial myocardial hypertrophy, ischemic heart disease, congenital dilated cardiomyopathy, myocarditis, etc. Heart failure can be caused by many factors, including ischemic, congenital, rheumatic and primary factors. Chronic cardiac hypertrophy is an obvious morbid state, and is a precursor to CHF and cardiac arrest.

"Myocardial infarction", as used herein, refers to patchy necrosis of some cardiac muscles induced by severe and persistent ischemia as a result of coronary artery occlusion or interruption of blood flow.

"Ordered and enhanced arrangement of sarcomere or sarcomere structure", as used herein, refers to a state in myocardial cells characterized by an orderly arrangement of contractile proteins that is displayed by α-actinin immunofluorescence staining. The orderly arrangement of α-actinin can be identified by a microscope and a photographic device connected to it. "Disorder or irregularity of sarcomere or sarcomere structure", as used herein, is the opposite of an "ordered and enhanced arrangement of sarcomere or sarcomere structure".

"Ordered or enhanced arrangement of cytoskeletal structure", as used herein, refers to a state in myocardial cells characterized by an orderly arrangement of actin filaments that is displayed by phalloidin staining. The orderly arrangement of actin filaments in cells can be identified by a microscope and a photographic device connected to it, as shown in the figures of this invention. "Disorder or irregularity of cytoskeletal structure", as used herein, is the opposite of an "ordered and enhanced arrangement of cytoskeletal structure".

"Protein", as used herein, has the same meaning as "polypeptide" or "peptide", unless otherwise expressly stated herein.

"Active unit" or "1 U", as used herein, refers to the dosage of a standard product capable of causing 50% maximum reaction. In other words, EC50 must be measured in order to determine the active unit of a certain active agent. For example, if the EC50 of a product is 0.067 μg/ml, the dosage is 1 unit. Further, if 1 μg of the product is used, it means that 14.93 U (1/0.067) is used. EC50 can be measured with any method known in the art, including the method used by the inventor in the following embodiments. The determination of the active unit is important for the quality control of genetic engineering products and drugs for clinical use, so that different pharmaceuticals and/or different batches of products can be quantified under the same standard.

In some embodiments, the unit of NRG is determined by measuring the activity of NRG through the kinase receptor activating enzyme-linked immunosorbent assay (KIRA-ELISA), as described in detail in WO03/099300 and Sadick et al., 1996, Analytical Biochemistry, 235: 207-14. The content is incorporated herein by reference in its entirety.

B. NRG Fusion Polypeptide

The present invention provides a number of NRG fusion polypeptide fragments. In some embodiments, the NRG fusion polypeptide comprises the EGF-like domain of NRG In some embodiments, the NRG fusion polypeptide comprises an EGF-like domain of a human NRG-02 isomer. In some embodiments, the NRG fusion polypeptide comprises an amino acid sequence of SEQ ID NO: 1. In some embodiments, the NRG fusion polypeptide comprises an amino acid sequence of an SEQ ID NO: 1 analogue thereof. In some embodiments, the NRG fusion polypeptide comprises an amino acid sequence of IgG Fc. In some embodiments, the NRG fusion polypeptide comprises an amino acid sequence of an IgG Fc analogue thereof. In some embodiments, the NRG fusion polypeptide comprises an amino acid sequence of IgG Fc. In some embodiments, the NRG fusion polypeptide comprises an amino acid sequence of IgG Fc analogs. In some embodiments, the NRG fusion polypeptide comprises an amino acid sequence of IgG1 Fc. In some embodiments, the NRG fusion polypeptide comprises an amino acid sequence of IgG4 Fc. In some embodiments, the NRG fusion polypeptide comprises an amino acid sequence of IgG1 Fc analogs. In some embodiments, the NRG fusion polypeptide comprises an amino acid sequence of IgG4 Fc analogs. In some embodiments, the NRG fusion polypeptide comprises an amino acid sequence of an IL-2 signal peptide, and an amino acid sequence of the IL-2 signal peptide is cleaved during extracellular secretion of the recombinantly prepared. In some embodiments, the NRG fusion polypeptide comprises an amino acid sequence of NRG EGF functional domain and IgG Fc. In some embodiments, the NRG fusion polypeptide comprises an amino acid sequence of the linker peptide, and the NRG EGF functional domain is fused with IgG Fc through the peptide linker. In some embodiments, the NRG fusion polypeptide comprises an amino acid sequence of SEQ ID NO: 2. In some embodiments, the NRG fusion polypeptide comprises an amino acid sequence of SEQ ID NO: 3.

In a more preferred embodiment, the NRG fusion polypeptide comprises an amino acid sequence of the EGF-like domain of NRG and an amino acid sequence of IgG Fc or Fc analogue thereof. In a more preferred embodiment, the NRG fusion polypeptide comprises an amino acid sequence of the IL-2 signal peptide, an amino acid sequence of the EGF-like domain of NRG and an amino acid sequence of IgG Fc or Fc analogue thereof, and the EGF-like domain of NRG is fused with IgG Fc through a peptide linker, and the amino acid sequence of the IL-2 signal peptide is cleaved during extracellular secretion of the recombinantly prepared. In a more preferred embodiment, the NRG fusion polypeptide comprises an amino acid sequence of SEQ ID NO: 1 of NRG, an amino acid sequence of IgG1 or IgG4 subtype Fc, and NRG is fused with IgG Fc through a peptide linker. In a more preferred embodiment, the NRG fusion polypeptide comprises an amino acid sequence of SEQ ID NO: 2. In a more preferred embodiment, the NRG fusion polypeptide comprises an amino acid sequence of SEQ ID NO: 3. In some embodiments, the present invention provides a method for treating heart failure by administering an effective dose of the NRG fusion polypeptide.

The NRG fusion polypeptide may be administered in the form of a pharmaceutical formulation.

A method for administering the NRG fusion polypeptide is determined by those skilled in the art, including but not limited to oral administration, intravenous injection, intragastric administration, rectal administration, intraperitoneal (intrapleural) administration and intracerebroventricular injection.

In a more preferred embodiment, the composition for administration is a pharmaceutical formulation. The pharmaceutical formulation can be one or more prophylactic or therapeutic agents containing a prophylactic or therapeutic dose (e.g., a compound containing the NRG fusion polypeptide and other prophylactic or therapeutic agents) and a pharmaceutically acceptable carrier or excipient. In one embodiment and herein, "pharmaceutically acceptable" means that a pharmaceutical formulation which has been approved by the relevant department of state or is documented in U.S. Pharmacopeia or other widely recognized Pharmacopeias is able to be used for animals, especially human being. "Carrier", as used herein, refers to diluent, adjuvant (e.g., Freund's complete adjuvant and incomplete adjuvant), excipient or any other carrier that aids the administration of a therapeutic agent. A drug carrier can be a sterile liquid, such as water and oil. The oil includes petroleum, animal oil, plant oil or synthetic oil, such as peanut oil, soybean oil, mineral oil, and sesame oil. The best carrier for intravenous injection of a pharmaceutical formulation is water. Saline, glucose and glycerol can be used to prepare a mixture for injection. An example of proper pharmaceutical carriers is described in E. W. Martin's *Remington's Pharmaceutical Scienices*.

A typical pharmaceutical formulation and dosage form contain one or more excipients. A suitable excipient, as is well known to those skilled in the pharmaceutical art, can include but be not limited to, starch, glucose, lactose, sucrose, gelatin, malt, rice, flour, chalk, silica gel, sodium stearate, glyceryl monostearate, mica, sodium chloride, dried skim milk, propylene, ethylene glycol, water and alcohol. Whether an excipient can be integrated into a pharmaceutical formulation or dosage form depends on lots of factors well known in the art, including but not limited to the way in which the dosage form is administered to a patient and the special active ingredient in the dosage form. As necessary, an agent or a single dosage form can contain a minute amount of wetting agent, emulsifier or pH buffer.

The pharmaceutical formulation contains an excipient well known in the art or an excipient published in, for example, the U.S. Pharmacopoeia (USP)SP(XXI)/NF(XVI). In general, a lactose-free agent contains an active ingredient, a binder/filler, and a pharmaceutically compatible lubricant in an acceptable dose. A typical lactose-free agent contains an active ingredient, microcrystalline cellulose, pre-gelatinized starch and magnesium stearate.

The pharmaceutical formulation and dosage form provided by the present invention contain one or more compounds that can reduce the decomposition rate of the active component. The compound, referred to as a "stabilizer" herein, comprises but is not limited to an antioxidant, such as an ascorbic acid, pH buffer or salt buffer.

The pharmaceutical formulation and single dosage form can exist in the form of a solution, suspension, emulsion, tablet, capsule, powder and sustained release. The oral agent contains a standard carrier such as pharmaceutical-grade mannitol, lactose, starch, magnesium stearate, saccharin sodium, cellulose or magnesium carbonate, etc. The pharmaceutical formulation and dosage form contain a prophylactic or therapeutic dose of a purified prophylactic or therapeutic agent, and may be mixed with a certain amount of carrier in order to function better in a patient. The pharmaceutical form should be suitable for the way of administration. In optimized embodiments, the pharmaceutical formulation or single dosage form should be sterile and administered in a proper form, preferably for animals, more preferably for mammals, and the most preferably for humans.

The form of a pharmaceutical formulation containing NRG fusion polypeptide should be suitable for its mode of administration. The modes of administration include but are not limited to injection (e.g., intravenous injection, intramuscular injection, subcutaneous injection or intracutaneous injection), oral administration, sublingual administration, inhalation, intranasal administration, percutaneous administration, topical administration, transmucous administration, intratumoral administration, intrasynovial administration, and rectal administration. In a particular embodiment, the pharmaceutical formulation can be produced by reference to a certain conventional procedure, such as a conventional procedure used to produce a pharmaceutical formulation for intravenous injection, intramuscular/subcutaneous injection, oral administration, intranasal administration or topical administration. In one embodiment, the form of the pharmaceutical formulation conforms to a conventional mode of subcutaneous injection administration. Typically, an agent administered by intravenous injection is a sterile isotonic solution. If necessary, the agent can also contain a solubilizer and a local anesthetic such as lignocaine to relieve pain at the injection site.

The dosage forms include but are not limited to tablets, caplets, capsules such as flexible gelatin capsules, cachets, pills, lozenges, dispersants, suppositories, ointment, cataplasms (poultices), paste, powder, dressings, emulsions, plaster, solutions, patches, aerosols (e.g., nasal sprays or inhalators), and colloids; the liquid dosage forms are suitable for oral administration or mucosal administration. The liquid dosage forms comprise suspension liquid (e.g., water or non-water suspension, oil-in-water emulsion or water-in-oil emulsion), solutions and cure-alls; the liquid dosage forms are suitable for injection administration; sterile solids (e.g., crystals or amorphous bodies) can be reconstructed into liquid dosage forms suitable for injection administration.

According to different uses, there is a difference in shape and dosage form among different agents containing the NRG fusion polypeptide. For example, dosage forms used for acute disorders may contain a larger amount of NRG fusion polypeptide than dosage forms used for long-term treatment of the same disease. Similarly, there is a difference among dosage forms effective in treating different cancers. Likewise, the amount of the active ingredient contained in the injectable dosage form is lower than that of the oral dosage form for treating the same disease or disorder. As is clear to those skilled in the art, the formulations described above, as well as other specific dosage forms contained in the present invention, differ from one another. See *Remington's Pharmaceutical Sciences*, edition 18, Mack Press, Easton, Pennsylvania (1990).

The NRG fusion polypeptide can be administered in any way recognized by those skilled in the art, including but not limited to oral administration, intravenous injection, intragastric administration, duodenal administration, intraperitoneal administration and intracerebroventricular injection.

C. Dosage and Routes of Administration

The dosage of the NRG fusion polypeptide provided by the present invention varies with the nature and severity of the disease or discomfort, as well as with the change of the route of administration for the active ingredient. The dosing frequency and dosage also vary from patient to patient due to specific personal factors, depending on specific treatment (e.g., a therapeutic or preventative agent), the severity of functional disorders, illness or discomfort, route of administration, age, body weight, reactions, and patient's medication history. An effective dose can be selected according to a dose-response curve obtained from an in-vitro or animal model test system.

Replicable dosage of the NRG fusion polypeptide comprises the milligrams or micrograms of NRG used per kilogram of body weight (e.g., about 1 microgram per kilogram of body weight about 500 milligram per kilogram of body weight, about 100 microgram per kilogram of body weight~about 5 milligram per kilogram of body weight, or 1 microgram per kilogram of body weight~about 50 microgram per kilogram of body weight). For example, 0.001 mg/kg-15 mg/kg of active peptide is used per kilogram of body weight. Suitable dosages also include 0.001 mg/kg-15 mg/kg, 0.005 mg/kg-10 mg/kg, 0.01 mg/kg-5 mg/kg, 0.001 mg/kg-4 mg/kg, 0.005 mg/kg-3 mg/kg, 0.01 mg/kg-2 mg/kg, 0.001 mg/kg-1 mg/kg, 0.005 mg/kg-0.5 mg/kg, 0.010 mg/kg-0.2 mg/kg, and 0.005 mg/kg-0.050 mg/kg.

Replicable dosage of the NRG fusion polypeptide also comprises the number of units (U) or unitage of NRG used per kilogram of body weight (e.g., about 1 U per kilogram of body weight~about 5,000 U per kilogram of body weight, about 10 U per kilogram of body weight~1,000 U per kilogram of body weight, or about 100 U per kilogram of body weight~500 U per kilogram of body weight). For example, 10 U/kg-1,000 U/kg of active peptide is used per kilogram of body weight. Suitable dosages also include 1 U/kg-10,000 U/kg, 1 U/kg-5,000 U/kg, 10 U/kg-5,000 U/kg, 10 U/kg-1,000 U/kg, 50 U/kg-2,000 U/kg, 50 U/kg-1,000

U/kg, 50 U/kg-500 U/kg, 100 U/kg-1,000 U/kg, 100 U/kg-500 U/kg, and 100 U/kg-200 U/kg.

In general, for the various diseases described herein, the daily dosage of the NRG fusion polypeptide recommended in the method provided by the present invention ranges from about 0.001 mg to 1,000 mg (based on the content containing NRG). In a particular situation, the daily total dosage can be 0.001 mg-15 mg, 0.005 mg-10 mg, 0.01 mg-5 mg, 0.001 mg-4 mg, 0.005 mg-3 mg, 0.01 mg-2 mg, 0.001 mg-1 mg, 0.005 mg-0.5 mg or 0.010 mg-0.2 mg. For case treatment, a low dose can be used at first, such as about 0.1 μg-1 μg per day, or about 20 μg-1, 000 μg per day if necessary, either in a single dose or in several times, depending on the patient's systematic response. In some cases, it is necessary for the dosage of the active ingredient to exceed the range described herein, and this is clear to those of ordinary skill in the art. In addition, it should be noted that a clinician or therapist should know how and when to interrupt, adjust or terminate treatment according to an individual patient's response. In some embodiments, the dosage of NRG is about 1 U/d~10, 000 U/d. In some embodiments, the dosage of NRG is about 1 U/d~5,000 U/d. In some embodiments, the dosage of NRG is about 10 U/d~2,000 U/d. In some embodiments, the dosage of NRG is about 10 U/d~1,000 U/d. In some embodiments, the dosage of NRG is about 100 U/d~200 U/d.

The NRG fusion polypeptide can also be administered according to a dosage schedule or "treatment cycle". The daily dosage for treatment is listed in detail above. Treatment can last 2 d, 5 d, 7 d, 10 d, 2 weeks, 3 weeks, 4 weeks, 5 weeks or 6 weeks.

In some embodiments, the NRG fusion polypeptide is used every day during the treatment cycle. In some embodiments, the NRG fusion polypeptide is used continuously for 3, 4, 5, 6, 7, 8, 9, 10, 11 or 12 d during a treatment cycle. In some embodiments, the NRG fusion polypeptide is used on the first day of a treatment cycle and is not used on the remaining day or days of the treatment cycle. In some embodiments, the NRG fusion polypeptide is used every day for 3, 5, 7 or 10 d during a treatment cycle and is not used for the rest of the treatment cycle. During a treatment cycle, the NRG fusion polypeptide needs to be used at a fixed interval of time, and the interval of time can be 1 d, 2 d, 3 d, 4 d, 5 d, 6 d, 7 d, 8 d, 9 d, 10 d, 11 d, 12 d, 13 d or 2 weeks~6 weeks.

EMBODIMENTS

Embodiment 1 Construction of a Vector for Expressing Fusion Polypeptide

A full-length DNA sequence containing human NRG (SEQ ID NO: 1), linkers and human immunoglobulin (IgG1 or IgG4) Fc fragments was subcloned to the pcDNA3.1 (+)

vector. A sequence containing the restriction enzyme Hind III site, Kozak sequence and melittin signal peptide was introduced at the 5' end, while a sequence containing the EcoRI site was introduced at the 3' end. After correct sequencing, it was transferred into E. coli through CaCl2 for amplification, with the plasmid preserved.

A DNA sequence containing IL-2-eGFP and IFN-eGFP was subcloned into the pcDNA3.1 (+) vector. A sequence containing the restriction enzyme Hind III site and Kozak sequence was introduced at the 5' end, while a sequence containing the EcoRI site was introduced at the 3' end. After correct sequencing, it was transferred into E. coli through CaCl2 for amplification, with the plasmid preserved.

A full-length DNA sequence containing human NRG (SEQ ID NO: 1), linkers and human immunoglobulin (IgG1 or IgG4) Fc fragments was subcloned to the pcDNA3.1 (+) vector. A sequence containing the restriction enzyme Hind III site, Kozak sequence and IL-2 signal peptide or IFN signal peptide sequence was introduced at the 5' end, while a sequence containing the EcoRI site was introduced at the 3' end. After correct sequencing, it was transferred into E. coli through CaCl2 for amplification, with the plasmid preserved.

Figure 1:
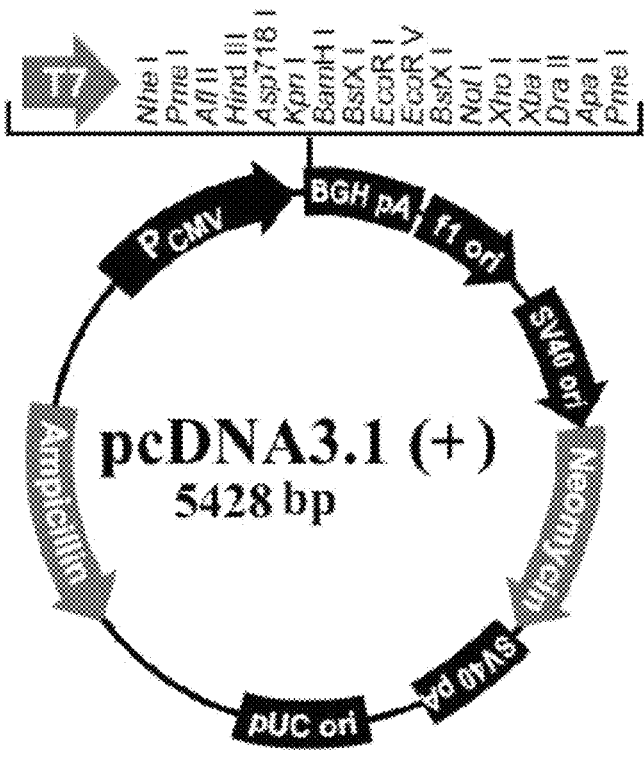
FIG. 1 is a schematic diagram of the expression vector
Figure 2:
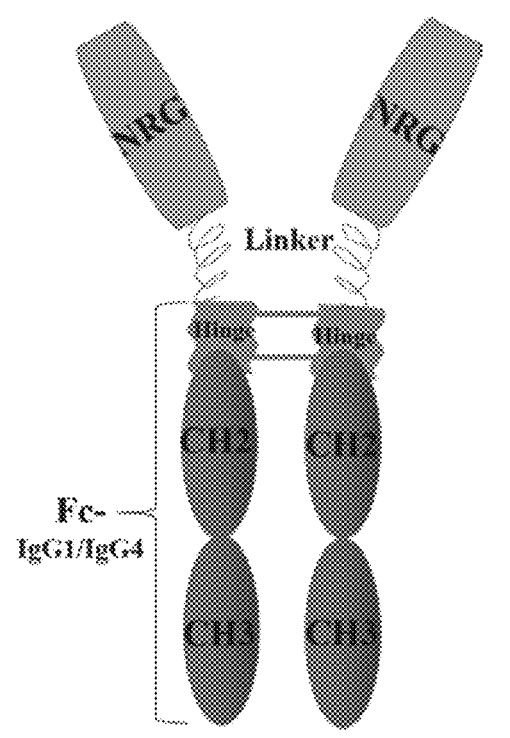
FIG. 2 is a schematic diagram of NRG-IgG1/IgG4-Fc fusion protein

For example, the above full-length DNA sequence containing NRG, linker peptide and human immunoglobulin (IgG1 or IgG4) Fc fragments has the corresponding amino acid sequence of SEQ ID NO: 2 and SEQ ID NO: 3. FIG. 1 shows vector constructed. FIG. 2 is a schematic diagram of NRG-IgG1/IgG4-Fc fusion protein.

Embodiment 2 Protein Expression and Detection

The correctly sequenced plasmid was transiently transfected into 293F cells. Preparation before transfection: 293F cells at the logarithmic growth phase, with activity >95%, were inoculated into a fresh SMM 293-TII culture medium mixed with 1% penicillin/streptomycin mixture, and the density was adjusted to 1.2-1.5*$10^6$ cells/ml, cultured for 24 h. On the day of transfection, the cell viability should be >90%, the cell density should be adjusted to 2.0-2.5×$10^6$ cells/mL, and the volume should be 20 mL.

Melittin-NRG-IgG1/IgG4-Fc and IFN-eGFP/IL-2-eGFP vector transfection: 30 ug of plasmid was taken and transfected according to the transfection reagent and method of Sinofection® (100 uL, Sino Biological). Feed was supplemented 24 h after transfection and every 48 h thereafter. At 37° C., 8% $CO_2$ orbital shake culture was performed at 120 rpm, with samples collected every 24 h. After sample collection, the expression of the target protein in the supernatant and cell lysis buffer was detected by SGS-PAGE and Western blot. The target protein was not detected in the cell lysis buffer or supernatant in the melittin-NRG-IgG1/IgG4-Fc expression system, indicating that NRG-IgG1/IgG4-Fc fusion polypeptide was not expressed in 293F cells when melittin was used as a signal peptide.

Figure 3:
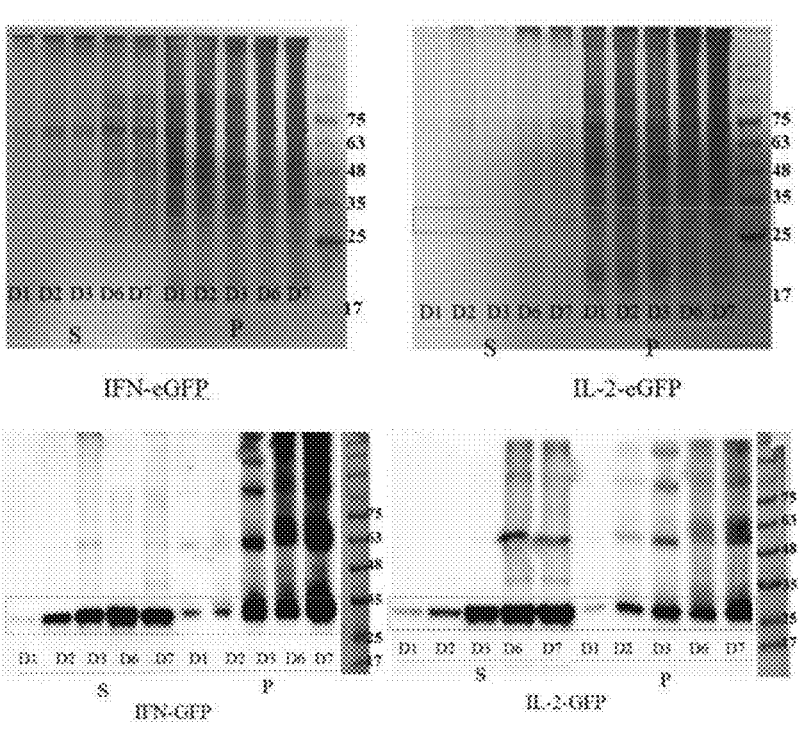
FIG. 3 shows the SDS-PAGE/Western blot results of expression in IFN/IL2-eGFP 293F

In contrast, when IFN/IL-2 was used as a signal peptide, the eGFP fusion polypeptide was highly expressed in 293F cells, and the IL2 signal peptide was significantly better than IFN in terms of the extracellular secretion efficiency of eGFP (see FIG. 3).

IL-2-NRG-IgG1/IgG4-Fc vector transfection: Plasmid DNA (30 ug and 45 ug) was mixed with 150 mM NaCl solution to 0.5 ml, and then let it stand for 5-10 min. The PEI solution with molecular weight of 40K was mixed with 150 mM NaCl solution to 0.5 mL, and then let it stand for 5-10 min. Then, PEI was mixed with DNA and incubated at room temperature for 20-30 min to form a DNA-PEI complex.

The transfection solution was added dropwise to the cell culture solution while the culture flask was shaken gently. Then, it was put back into the shaker for further culture. Feed was supplemented 24 h after transfection and every 48 h thereafter. At 37° C., 8% $CO_2$ orbital shake culture was performed, and samples were taken every 24 h to detect the cell transfection efficiency. According to the expression characteristics of different proteins, samples could be collected as long as 6-10 d after transfection. The supernatant was collected by centrifugation and stored at −20° C.

Figure 4:
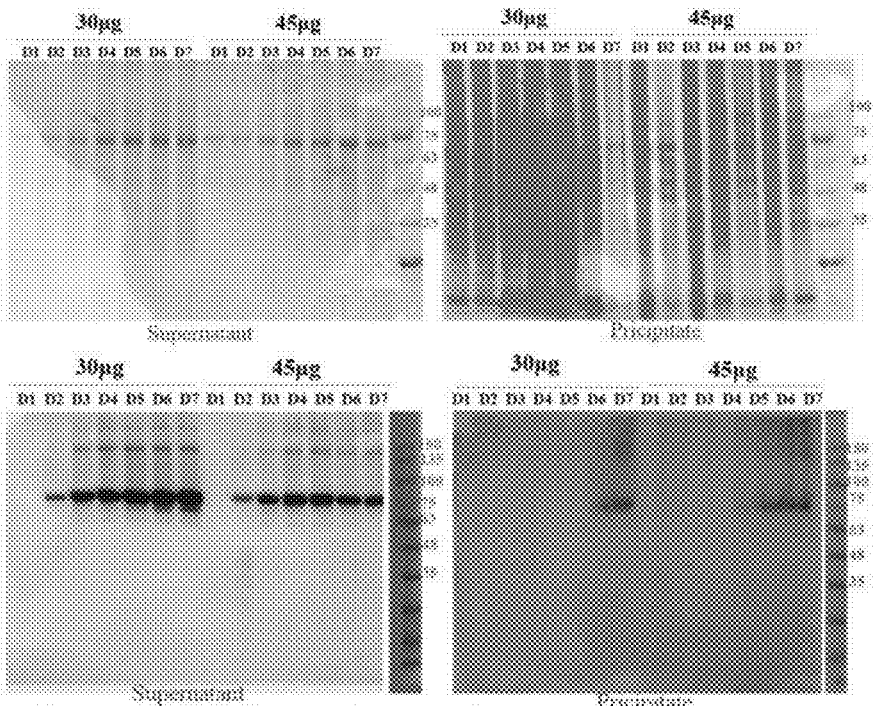
FIG. 4 shows the SDS-PAGE/Western blot results of expression in IL2-NRG-IgG1-Fc 293F

Samples with different DNA/PEI mass ratios were taken at different time points to detect the expression by SDS-PAGE and Western-blot analysis (see FIG. 4 for the results) to determine optimum conditions for transfection and sample collection.

Embodiment 3 Purification of Fusion Protein

Figure 5:
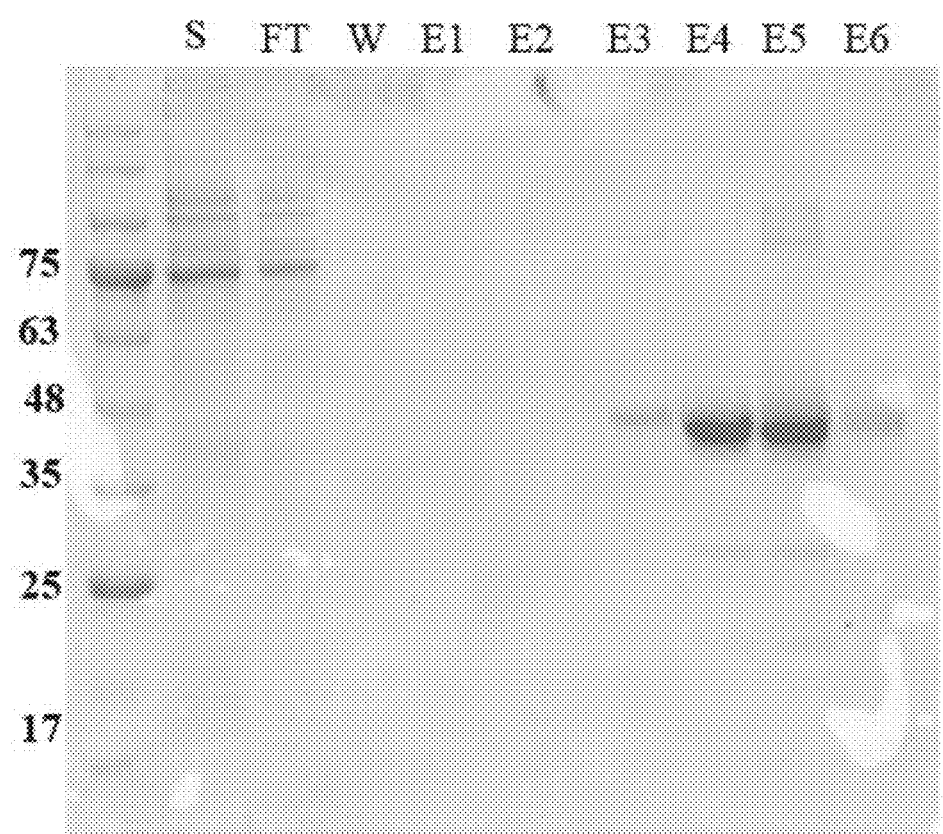
FIG. 5 shows the SDS-PAGE results of purified NRG-IgG1-Fc fusion polypeptide (in reduced state)

An equal volume of binding buffer (0.02M of disodium hydrogen phosphate, pH 7.0) was added to the supernatant, with the pH value adjusted to 7.0. Samples could also be pretreated in a dialysis system or desalting column. Then, the supernatant was first filtered through a 1 um filter head, then through a 0.45 um filter membrane, and finally through an affinity column. Samples at peak value of OD280 were collected and tested by SDS-PAGE (see FIG. 5 for the results).

Embodiment 4 Binding of a Receptor to NRG Polypeptide

MCF-7 cells were collected, counted, centrifuged and re-suspended in DMEM (10% serum, 9 μg/ml of insulin), at a cell density of $5×10^4$/ml. A 96-well plate was spread. 100 μl of suspension was put in each well and left standing overnight at 37° C. The cells were washed with PBS three times the next day, and cultured in serum-free DMEM for 24 h.

The ErbB2 antibody H4 was diluted with a coating buffer (50 mM $Na_2CO_3$—$NaHCO_3$, pH9.6) to 4 μg/ml, and put in a 96-well plate, with 50 μl in each well, and then left standing overnight at 4° C. so that the antibody can bind to the plate.

The DMEM medium in MCF-7 cells was sucked out. Then, NRG and NRG-IgG1-Fc were diluted with DMEM serially and then put in the wells, with 100 μl in each well. Here, NRG was a recombinant NRG polypeptide with an amino acid sequence of SEQ ID NO: 1, and NRG-IgG1-Fc was a recombinant NRG fusion protein with an amino acid sequence of SEQ ID NO: 2. Only DMEM was added to the blank control. After being incubated at 37° C. for 20 min, the cells were washed with PBS buffer. Then, 100 μl/well of lysis buffer (50 mM Hepes, pH8.0, 150 mM NaCl, 2 mM sodium orthovanadate, 0.01% thimerosal, 1% Triton X-100 and 25 ml of protease inhibitor cocktail) was added to each well, lysed at 4° C. for 30 min. Then, the plate was shaken gently to remove the cells from the plate, with it centrifuged at 15,000 rpm for 15 min.

The antibody-coated plate was washed with washing liquid (10 mM PBS, pH7.4, 0.05% Tween 20) for 5 times. 200 μl of washing liquid containing 5% skimmed milk was added to each well, incubated at 37° C. for 2 h, and then washed with washing liquid for 3 times.

The lysed cell sap was added to the coated plate, with 90 μl in each well, incubated at 37° C. for 1 hour, and then washed with washing liquid for 5 times. 100 μl of horseradish peroxidase (HRP) with proper concentration was added to it, incubated at 37° C. for 1 hour. After washing 5 times, a fresh prepared HRP substrate solution ((50 mM citric acid, 100 mM $Na_2HPO_4$, pH 5.0, 0.2 mg/ml of tetramethylbenzidine (TMB, 0.003% $H_2O_2$) was added, incubated at 37° C. for 10 min. Finally, 50 μl 1M $H_2SO_4$ was added to each well to destroy HRP activity to terminate the reaction. The OD value of each well was measured at 450 nm on a microplate reader. EC50 was the concentration of NRG or fusion protein reaching the midpoint of maximum absorbance. The lower the EC50 value was, the higher the affinity of the receptor to NRG or fusion protein was.

Table 1 and 2 show the EC50 values of NRG NRG-IgG1-Fc and NRG-IgG4-Fc. The EC50 values of NRG-IgG1-Fc and NRG-IgG4-Fc are slightly higher than that of NRG

TABLE 1

| EC50 Values of NRG and NRG-IgG1-Fc | |
| --- | --- |
| Samples | $EC_{50}(nM)$ |
| NRG | 0.9245 |
| NRG-IgG1-Fc | 2.483 |

TABLE 2

| EC50 Values of NRG and NRG-IgG4-Fc | |
| --- | --- |
| Samples | $EC_{50}(nM)$ |
| NRG | 1.651 |
| NRG-IgG4-Fc | 3.659 |

Embodiment 5 ELISA Method Used to Detect the Half-Life Period of Intravenously or Subcutaneously Injected NRG-IgG1-F and NRG-IgG4-Fc Fusion Peptides in Rats Rats were injected with 250 ug/kg of NRG-IgG1-Fc through the tail vein or 500 ug/kg of NRG-IgG1-Fc subcutaneously or 250 ug/kg of NRG-IgG4-Fc through the tail vein. Then, blood was collected from the jugular vein at different time points after administration. Let it stand at room temperature for at least 30 min. It was centrifuged after blood coagulation to collect the supernatant. The rat serum containing NRG-IgG1-Fc was diluted with dilution buffer in a ratio of 1:1 for later use.

Standard NRG-IgG1-Fc samples were prepared with rat serum in a concentration range of 5,000 ng/ml, 2,500 ng/ml, 1,000 ng/ml, 200 ng/ml, 40 ng/ml, 8 ng/ml, 1.6 ng/ml, 0.32 ng/ml, 0.064 ng/ml and 0 ng/ml, and then diluted with dilution buffer in a ratio of 1:1.

Plate coating and blocking: Human NRG1/HRG1-β1 EGF domain antibody was diluted with a coating buffer, and coated overnight at 4° C. after adding 50 uL to each reaction well in a 96-well plate. The coating buffer was discarded the next day, while the plate was washed, and a block buffer was added to it for blocking at room temperature. After the plate was dried on a piece of absorbent paper, 50 uL of corresponding standard sample or sample to be tested was added to each reaction well, and incubated at room temperature for 2 h. The plate was washed. Then, Anti-Human IgG1 Fc (HRP) antibody was added to it, and incubated at room temperature for 1 hour. The plate was washed. Then, temporarily prepared TMB substrate solution was added to each reaction well. After 20 min of photophobic reaction at 37° C., 50 uL 1M of sulfuric acid was added to terminate the reaction. The absorbance of each reaction well at 450 nM was measured, and the content of NRG and protein in the sample was calculated according to the standard curve. The data were analyzed using GraphPad Prism 5.0.

The results are shown in Tables 3, 4 and 5, respectively:

TABLE 3

Half-life results of intravenously injected NRG-IgG1-Fc

| Parameters | Unit | Mean |
|---|---|---|
| $AUC_{(0-t)}$ | ng/ml*h | 104777.97 |
| $T_{(1/2)}$ | h | 4.66 |
| $CL_{z/F}$ | L/h/kg | 0.00 |
| $C_{max}$ | ng/ml | 34148.32 |

TABLE 4

Half-life results of subcutaneously injected NRG-IgG1-Fc

| Parameters | Unit | Mean |
|---|---|---|
| $AUC_{(0-t)}$ | ng/ml*h | 6330.97 |
| $T_{(1/2)}$ | h | 13.45 |
| $CL_{z/F}$ | L/h/kg | 0.08 |
| $C_{max}$ | ng/ml | 282.33 |

TABLE 5

Half-life results of intravenously injected NRG-IgG4-Fc

| Parameters | Unit | Mean |
|---|---|---|
| $AUC_{(0-t)}$ | ng/ml*h | 38034.83 |
| $T_{(1/2)}$ | h | 8.48 |
| $CL_{z/F}$ | L/h/kg | 0.01 |
| $C_{max}$ | ng/ml | 9816.47 |

The experimental data showed that compared with the 10 min half-life period of intravenously injected NRG and 1.5 h half-life period of subcutaneously injected NRG, the fusion peptides NRG-IgG1-Fc and NRG-IgG4-Fc could significantly prolong the half-life of NRG fragments injected intravenously and subcutaneously into rats.

Embodiment 6 Pharmacodynamic Experiment of Intravenously Injected NRG-IgG1-Fc Fusion Polypeptide in Treating Rats with Heart Failure 6.1 Experimental Objectives In the rat model of heart failure induced by left coronary artery ligation, rats were injected intravenously with NRG-IgG1-Fc fusion protein once a day and injected intravenously with recombinant human NRG (rhNRG) in a sustained way through a Medtronic insulin injection pump to compare the therapeutic effects of four administration methods on the rat model of heart failure.

6.2 Experimental Materials 6.2.1 Experimental Animals 6.2.1.1 Strain & source: Wistar rat, provided by Shanghai Sippe-Bk Lab Animal Co., Ltd.

6.2.1.2 Gender, weight and number: male, 200-250 g, 150

6.2.2 Reagents 6.2.2.1 Excipient: Developed by Zensun (Shanghai) Sci & Tech Co., Ltd. Dosage form: freeze-dried powder; specification: 2 mg Alb/bottle 6.2.2.2 Recombinant human NRG: Developed by Zensun (Shanghai) Sci & Tech Co., Ltd. Dosage form: freeze-dried powder; specification: 250 μg/piece 6.2.2.3 Recombinant human NRG-IgG1-Fc fusion protein: Developed by Zensun (Shanghai) Sci & Tech Co., Ltd. Dosage form: injection 6.2.2.4 Isoflurane: RWD Life Technology Co., Ltd.

6.3 Experimental Equipment 6.3.1 Anesthesia apparatus (isoflurane evaporator): MSS INTERNATIONAL LTD 6.3.2 Ultrasonic heart detector: Vivid E95; probe type: 12S-D 6.3.3 Insulin pump: Medtronic; model: MMT-712EWS, MMT-722NAS/L 6.3.4 PowerLab multi-channel physiological recorder: ADInstruments (Shanghai) Co., Ltd.; model: ML-845

6.4 Experimental Methods 6.4.1 Establishment of a Rat Model of Heart Failure Induced by Coronary Artery Ligation Rats were anesthetized with 4% isoflurane in a gas anesthesia apparatus, and then fixed in supine position and sterilized with 75% alcohol after chest hair removal. After the left anterior chest skin was cut open, the chest muscles were bluntly dissected, with the $4^{th}$ and $5^{th}$ ribs exposed. The muscles between the $4^{th}$ and $5^{th}$ ribs were bluntly dissected with hemostatic forceps, squeezed with both hands, so that the heart was squeezed out of the thoracic cavity and fully exposed. Lung inflation and heartbeat were put under observation. The left atrial appendage and pulmonary arterious cone were fully exposed, and between them, the left anterior descending coronary artery was ligated with 6-0 sutures. Then, the chest was squeezed hard to discharge air, and then the chest muscles and skin were sutured. After surgery, the rats were put back into the cage and placed under close observation. In case of acute arrhythmia, the heart was massaged urgently for 3-5 min. After the operation, 80,000 U of penicillin sodium was injected intramuscularly into each rat's muscles for 2 d.

6.4.2 Grouping and Drug Administration 6.4.2.1 Grouping

The grouping results are shown in Table 6. At week 2 and 4 after surgery, the rats' cardiac function was detected by B-ultrasound Vivid E95. After cardiac ultrasound at week 4, rats with EF value of 28%-45% were selected for the next experiment.

TABLE 6

Experimental animal grouping and administration arrangement

| Group | Dosage | Dosing Volume | Dose Concentration | Route of Administration | Cycle of Administration |
|---|---|---|---|---|---|
| Model Group | — | 2 ml/kg each time | — | Intravenous injection | Qd × 10 d |
| NRG-IgG1-Fc Group | 10 ug/kg | 2 ml/kg each time | 5 ug/ml | Intravenous injection | Qd × 10 d |

TABLE 6-continued

| | | | | | |
|---|---|---|---|---|---|
| | | | Experimental animal grouping and administration arrangement | | |
| Group | Dosage | Dosing Volume | Dose Concentration | Route of Administration | Cycle of Administration |
| NRG-IgG1-Fc Group | 30 ug/kg | 2 ml/kg each time | 15 ug/ml | Intravenous injection | Qd × 10 d |
| NRG Group | 6 ug/kg | 5 ml/kg | 1.2 ug/ml | Tail vein infusion | 8 h/d × 10 d |
| Sham Operation Group | — | — | — | — | — |

The rats were randomly divided into 4 groups according to the results of cardiac ultrasound. The rats that received an intravenous injection were divided into the excipient group, the NRG-IgG1-Fc 30 μg/kg qid group, and the NRG-IgG1-Fc 6 μg/kg qid group. According to Table 1, intravenous injection was performed every day for 10 d, and the dose volume was set to 2 ml/kg/time, while the dose concentration was set to 5 μg/ml and 15 μg/ml respectively.

The NRG tail vein group was treated with an insulin pump for 8 h a day and for 10 d; the dosing volume was 5 ml/kg, the dosage of NRG was 6 μg/kg and the concentration was 1.2 μg/ml.

The sham operation group underwent threading only rather than coronary artery ligation and medication.

6.4.2.2 Dispensing Methods

1) Excipient: 2 mg Alb/bottle, with 1 ml of normal saline added to each bottle to prepare mother liquor, and 0.24 ml of mother liquor was diluted with 49.76 ml of normal saline into 9.6 μg/ml of Alb solution.

2) NRG-IgG1-Fc: 0.4 mg-0.8 mg/ml of NRG-IgG1-Fc mother liquor was diluted with normal saline into NRG-IgG1-Fc with a certain working concentration.

3) NRG: 250 μg NRG/bottle, with 1 ml of normal saline added to each bottle to prepare mother liquor, and 0.24 ml of mother liquor was diluted with 49.76 ml normal saline into 1.2 μg/ml of NRG solution.

6.4.3 Observation Indexes 6.4.3.1 Cardiac Function Test

After being anesthetized with 4% isoflurane in the gas anaesthesia apparatus, the rats were fixed to a surgical stent in left recumbent position. The rat head was fixed in the breathing mask of the gas anaesthesia apparatus, with the concentration of isoflurane maintained at 2%. After chest hair removal and sterilization with 75% alcohol, the rats were smeared with a couplant, and then a rat cardiac ultrasound probe was used to test the left ventricular echo signal. In "B-mode", the cardiac ultrasound probe was placed near the left side of the sternum with the probe pointing to 2-3 o'clock. The sound beam cut the heart in the direction perpendicular to the long axis of the heart. The probe was adjusted until it became horizontally parallel to both papillary muscles to obtain a horizontal left ventricular short axis view of the papillary muscles to collect a dynamic image of the papillary muscle of left ventricle and save it. In "M-mode", the probe was kept on the left ventricular short axis section, and the M-mode sampling line was adjusted so that it could pass through the weakest point of heartbeat on the anterior wall. The focal length was adjusted, and an M-shaped curve (the left ventricular cavity and the anterior and posterior walls of the left ventricle should be clearly displayed) was used to measure the left ventricular end diastolic diameter (D) and left ventricular end systolic diameter (D). The left ventricular end-diastolic volume (EDV) and end-systolic volume (ESV) were calculated by Teichholtz's formula $V=7/(2.4+D)*D$ 3. Also, the ejection fraction (EF) was calculated as follows: $EF=(EDV-ESV)/EDV*100\%$.

6.4.3.2 Hemodynamic Test of Heart

A physiological recorder was used to record hemodynamic indexes such as carotid arterial pressure, intraventricular pressure, +dp/dt and −dp/dt. Main steps: The rats were anesthetized by intraperitoneal injection of 20% urethane, with an injection volume of 6 ml/kg. The right common carotid artery was separated, and its distal end was ligated. Its proximal end was blocked with an artery clamp, and a small opening was cut between both ends. Then, the PE50 catheter connected with the probe was inserted into the common carotid artery through the opening. The waveform displayed by the Powerlab physiological recorder was observed. After stabilization, the carotid artery pressure was recorded, and then the catheter was further inserted into the left ventricle for 10-min indwelling. After stabilization, the indexes such as LVSP, LVEDP, +dp/dt and −dp/dt were recorded, and LabChart7 was used for analysis.

6.4.4 Data Processing

All experimental data were expressed in $\bar{x}\pm SD$. GraphPad Prism 6 was used for one-way ANOVA analysis. $P<0.05$ indicated that there was a significant difference between the groups, while $P<0.01$ indicated that there was an extremely significant difference between the groups.

6.5 Experimental Results

Figure 6:
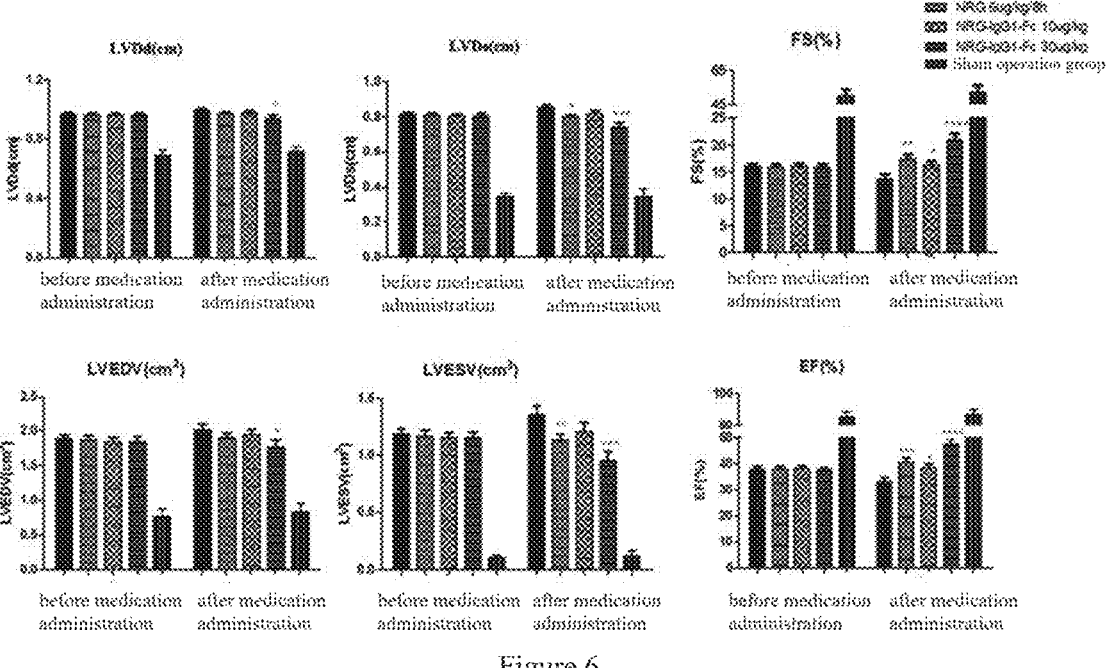
FIG. 6 shows the echocardiographic results of all rats with heart failure before and after medication administration

The results of cardiac ultrasound are shown in Table 7 and FIG. 6. The experimental results showed that after random grouping of heart failure rats, there was no significant difference in cardiac ultrasound data between the groups before administration. After administration, there were obvious differences between the groups. 10 d of injection of NRG-IgG1-Fc (30 ug/kg a day) could significantly increase the EF and FS values ($P<0.001$) of the rat heart, and significantly decrease the values of LVESV ($P<0.001$), LVEDV ($P<0.05$), LVDs ($P<0.001$) and LVDd ($P<0.05$), suggesting that it could significantly improve the cardiac function of rats with heart failure. After continuous infusion for 8 h*10 d, the EF, LVESV, FS and LVDs values of the NRG group were improved. The results showed that an equimolar amount (30 ug/kg) of NRG-IgG1-Fc produced a better therapeutic effect on heart failure in rats in the treatment group than the NRG group. Moreover, NRG-IgG1-Fc was easier to use than NRG.

TABLE 7

| | Results of cardiac ultrasound in rats before and after treatment of each group | | | | | | | |
|---|---|---|---|---|---|---|---|---|
| | Model Group | | NRG (6 ug/kg/8 h) | | NRG-IgG1-Fc (10 ug/kg) | | NRG-IgG1-Fc (30 ug/kg) | |
| | Pre-Administration | Post-Administration | Pre-Administration | Post-Administration | Pre-Administration | Post-Administration | Pre-Administration | Post-Administration |
| LVDd (cm) | 0.969 ± 0.035 | 0.99 ± 0.058 | 0.963 ± 0.049 | 0.97 ± 0.046 | 0.96 ± 0.044 | 0.977 ± 0.058 | 0.959 ± 0.055 | 0.94 ± 0.086* |
| LVDs (cm) | 0.814 ± 0.042 | 0.855 ± 0.066 | 0.81 ± 0.048 | 0.801 ± 0.047* | 0.806 ± 0.045 | 0.819 ± 0.067 | 0.806 ± 0.051 | 0.744 ± 0.097*** |
| LVEDV (cm³) | 1.896 ± 0.186 | 2.02 ± 0.308 | 1.868 ± 0.25 | 1.905 ± 0.242 | 1.85 ± 0.22 | 1.934 ± 0.317 | 1.85 ± 0.276 | 1.768 ± 0.414* |
| LVESV (cm³) | 1.183 ± 0.168 | 1.359 ± 0.277 | 1.166 ± 0.175 | 1.133 ± 0.18** | 1.15 ± 0.175 | 1.21 ± 0.268 | 1.154 ± 0.19 | 0.95 ± 0.106*** |
| FS % | 16 ± 2.1 | 13.8 ± 3.1 | 15.9 ± 1.9 | 17.4 ± 3.5** | 16.1 ± 2.0 | 16.3 ± 2.8* | 16 ± 2.0 | 21.1 ± 1.9*** |
| EF % | 37.8 ± 4.4 | 33.0 ± 6.5 | 37.7 ± 3.9 | 40.4 ± 6.8*** | 38 ± 4.2 | 38.3 ± 5.7* | 37.7 ± 4.1 | 47.4 ± 7.0**** |

The scope of the present invention is not limited to the embodiments. As is clear to those skilled in the art, the present invention can be modified and changed in many manners without departing from its spirit and scope. The embodiments described herein are provided in the form of embodiments only, and the present invention is subject only to the appended claims and their equivalents in their entirety.

SEQUENCE LISTING

<160> NUMBER OF SEQ ID NOS: 5

<210> SEQ ID NO 1
<211> LENGTH: 61
<212> TYPE: PRT
<213> ORGANISM: Homo sapiens

<400> SEQUENCE: 1

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

<210> SEQ ID NO 2
<211> LENGTH: 308
<212> TYPE: PRT
<213> ORGANISM: Artificial Sequence
<220> FEATURE:
<223> OTHER INFORMATION: NRG fusion polypeptide comprises an amino acid
      sequence of the linker peptide, and the EGF-like domain of NRG is
      fused with IgG Fc through the peptide linker

<400> SEQUENCE: 2

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln Gly Gly Gly
    50                  55                  60

Gly Ser Gly Gly Gly Gly Ser Gly Gly Gly Gly Ser Glu Pro Lys Ser
```

```
65                  70                  75                  80

Cys Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
               100                 105                 110

Met Ile Ser Arg Thr Pro Glu Val Thr Cys Val Val Val Asp Val Ser
               115                 120                 125

His Glu Asp Pro Glu Val Lys Phe Asn Trp Tyr Val Asp Gly Val Glu
           130                 135                 140

Val His Asn Ala Lys Thr Lys Pro Arg Glu Glu Gln Tyr Asn Ser Thr
       145                 150                 155                 160

Tyr Arg Val Val Ser Val Leu Thr Val Leu His Gln Asp Trp Leu Asn
                   165                 170                 175

Gly Lys Glu Tyr Lys Cys Lys Val Ser Asn Lys Ala Leu Pro Ala Pro
               180                 185                 190

Ile Glu Lys Thr Ile Ser Lys Ala Lys Gly Gln Pro Arg Glu Pro Gln
               195                 200                 205

Val Tyr Thr Leu Pro Pro Ser Arg Glu Glu Met Thr Lys Asn Gln Val
       210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                   245                 250                 255

Pro Val Leu Asp Ser Asp Gly Ser Phe Phe Leu Tyr Ser Lys Leu Thr
               260                 265                 270

Val Asp Lys Ser Arg Trp Gln Gln Gly Asn Val Phe Ser Cys Ser Val
       275                 280                 285

Met His Glu Ala Leu His Asn His Tyr Thr Gln Lys Ser Leu Ser Leu
       290                 295                 300

Ser Pro Gly Lys
305

<210> SEQ ID NO 3
<211> LENGTH: 307
<212> TYPE: PRT
<213> ORGANISM: Artificial Sequence
<220> FEATURE:
<223> OTHER INFORMATION: NRG fusion polypeptide comprises an amino acid
      sequence of the linker peptide, and the EGF-like domain of NRG is
      fused with IgG Fc through the peptide linker

<400> SEQUENCE: 3

Ser His Leu Val Lys Cys Ala Glu Lys Glu Lys Thr Phe Cys Val Asn
1               5                  10                  15

Gly Gly Glu Cys Phe Met Val Lys Asp Leu Ser Asn Pro Ser Arg Tyr
                20                  25                  30

Leu Cys Lys Cys Pro Asn Glu Phe Thr Gly Asp Arg Cys Gln Asn Tyr
           35                  40                  45

Val Met Ala Ser Phe Tyr Lys Ala Glu Glu Leu Tyr Gln Gly Gly Gly
       50                  55                  60

Gly Ser Gly Gly Gly Gly Ser Gly Gly Gly Gly Ser Glu Ser Lys Tyr
65                  70                  75                  80

Gly Pro Pro Cys Pro Pro Cys Pro Ala Pro Glu Phe Glu Gly Gly Pro
                85                  90                  95

Ser Val Phe Leu Phe Pro Pro Lys Pro Lys Asp Thr Leu Met Ile Ser
               100                 105                 110
```

```
Arg Thr Pro Glu Val Thr Cys Val Val Val Asp Val Ser Gln Glu Asp
        115                 120                 125

Pro Glu Val Gln Phe Asn Trp Tyr Val Asp Gly Val Glu Val His Asn
    130                 135                 140

Ala Lys Thr Lys Pro Arg Glu Glu Gln Phe Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Gly Leu Pro Ser Ser Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Gln Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Arg Leu Thr Val Asp Lys
            260                 265                 270

Ser Arg Trp Gln Glu Gly Asn Val Phe Ser Cys Ser Val Met His Glu
        275                 280                 285

Ala Leu His Asn His Tyr Thr Gln Lys Ser Leu Ser Leu Ser Leu Gly
    290                 295                 300

Lys Ala Ser
305
```

```
<210> SEQ ID NO 4
<211> LENGTH: 20
<212> TYPE: PRT
<213> ORGANISM: Artificial Sequence
<220> FEATURE:
<223> OTHER INFORMATION: IL-2 signal peptide

<400> SEQUENCE: 4

Met Tyr Arg Met Gln Leu Leu Ser Cys Ile Ala Leu Ser Leu Ala Leu
1               5                   10                  15

Val Thr Asn Ser
            20
```

```
<210> SEQ ID NO 5
<211> LENGTH: 15
<212> TYPE: PRT
<213> ORGANISM: Artificial Sequence
<220> FEATURE:
<223> OTHER INFORMATION: liner peptide

<400> SEQUENCE: 5

Gly Gly Gly Gly Ser Gly Gly Gly Ser Gly Gly Gly Gly Ser
1               5                   10                  15
```

The invention claimed is:

1. A Neuregulin (NRG) fusion polypeptide comprising the amino acid sequence of SEQ ID NO: 2 or SEQ ID NO: 3.

2. A pharmaceutical formulation, comprising the NRG fusion polypeptide of claim 1 and a pharmaceutically acceptable carrier, excipient or diluent.

* * * * *